(12) United States Patent
Feld et al.

(10) Patent No.: US 7,922,754 B2
(45) Date of Patent: Apr. 12, 2011

(54) APPARATUS AND METHODS FOR DELIVERING PROSTHESES TO LUMINAL BIFURCATIONS

(75) Inventors: Tanhum Feld, Moshav Merhavya (IL); Eitan Konstantino, Orinda, CA (US)

(73) Assignee: Trireme Medical, Inc., Pleasanton, CA (US)

( * ) Notice: Subject to any disclaimer, the term of this patent is extended or adjusted under 35 U.S.C. 154(b) by 1229 days.

(21) Appl. No.: 11/406,139

(22) Filed: Apr. 17, 2006

(65) Prior Publication Data

US 2006/0259116 A1    Nov. 16, 2006

Related U.S. Application Data

(60) Provisional application No. 60/758,726, filed on Jan. 12, 2006, provisional application No. 60/672,735, filed on Apr. 18, 2005.

(51) Int. Cl.
*A61F 2/82* (2006.01)
*A61M 29/00* (2006.01)

(52) U.S. Cl. ....... 623/1.11; 606/108; 606/191; 606/194; 606/195

(58) Field of Classification Search .................. 623/1.11; 606/191, 108, 194, 195, 198
See application file for complete search history.

(56) References Cited

U.S. PATENT DOCUMENTS

| | | | |
|---|---|---|---|
| 4,994,071 A | 2/1991 | MacGregor | |
| 5,609,627 A | 3/1997 | Goicoechea et al. | |
| 5,749,825 A | 5/1998 | Fischell et al. | |
| 5,755,735 A | 5/1998 | Richter et al. | |
| 5,928,248 A | 7/1999 | Acker | |
| 5,997,468 A | 12/1999 | Wolff et al. | |
| 6,048,361 A | 4/2000 | Von Oepen | |
| 6,099,497 A | 8/2000 | Adams et al. | |
| 6,165,195 A * | 12/2000 | Wilson et al. | 606/194 |
| 6,210,429 B1 | 4/2001 | Vardi et al. | |
| 6,221,098 B1 | 4/2001 | Wilson et al. | |
| 6,325,826 B1 | 12/2001 | Vardi et al. | |
| 6,596,020 B2 | 7/2003 | Vardi et al. | |
| 6,599,316 B2 | 7/2003 | Vardi et al. | |
| 6,676,691 B1 | 1/2004 | Hosny | |
| 6,682,536 B2 | 1/2004 | Vardi et al. | |
| 6,689,156 B1 | 2/2004 | Davidson et al. | |
| 6,692,483 B2 | 2/2004 | Vardi et al. | |

(Continued)

FOREIGN PATENT DOCUMENTS

DE    29 708 803 U1    7/1997

(Continued)

OTHER PUBLICATIONS

International Searcg Report of EP Application No. 06750644.4, dated Dec. 4, 2009, 3 pages total.

*Primary Examiner* — Vy Q Bui

(74) *Attorney, Agent, or Firm* — Kilpatrick Townsend & Stockton LLP

(57) ABSTRACT

A catheter for delivering luminal prostheses comprises a catheter body having an expandable member near a distal end. The prosthesis has a side hole, and a guidewire extends beneath a proximal portion of the prosthesis and over the exterior of the expandable member. A distal end of the guidewire is retracted proximally from the closest point on the side opening to reduce possible interference with catheter advancement.

16 Claims, 13 Drawing Sheets

U.S. PATENT DOCUMENTS

| | | |
|---|---|---|
| 6,706,062 B2 | 3/2004 | Vardi et al. |
| 6,709,440 B2 | 3/2004 | Calloi et al. |
| 6,712,783 B1 | 3/2004 | Jang |
| 6,835,203 B1 | 12/2004 | Vardi et al. |
| 6,884,258 B2 | 4/2005 | Vardi et al. |
| 2002/0042650 A1 | 4/2002 | Vardi et al. |
| 2002/0156516 A1 | 10/2002 | Vardi et al. |
| 2002/0173835 A1 | 11/2002 | Bourang et al. |
| 2003/0055377 A1 | 3/2003 | Sirhan et al. |
| 2003/0187494 A1 | 10/2003 | Loaldi |
| 2003/0195606 A1 | 10/2003 | Davidson et al. |
| 2004/0015227 A1 | 1/2004 | Vardi et al. |
| 2004/0019302 A1 | 1/2004 | Williams et al. |
| 2004/0133268 A1 | 7/2004 | Davidson et al. |
| 2004/0138737 A1 | 7/2004 | Davidson et al. |
| 2005/0010278 A1 | 1/2005 | Vardi et al. |
| 2005/0015108 A1 | 1/2005 | Williams et al. |
| 2005/0060027 A1 | 3/2005 | Khenansho et al. |
| 2005/0102019 A1 | 5/2005 | Yadin |
| 2006/0036315 A1 | 2/2006 | Yadin et al. |

FOREIGN PATENT DOCUMENTS

| | | |
|---|---|---|
| DE | 29 701 758 U1 | 3/1999 |
| EP | 0 897 700 A1 | 2/1999 |
| EP | 1255506 B1 | 11/2002 |

* cited by examiner

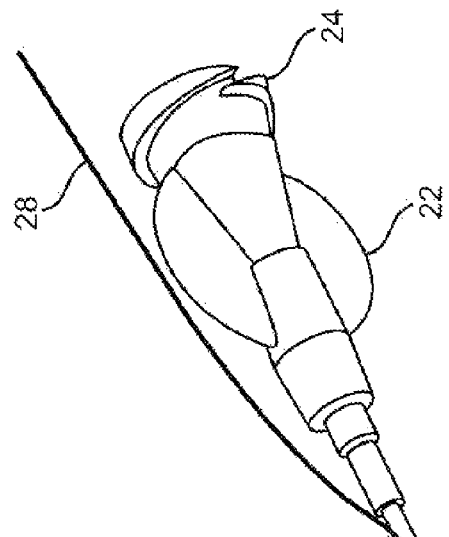
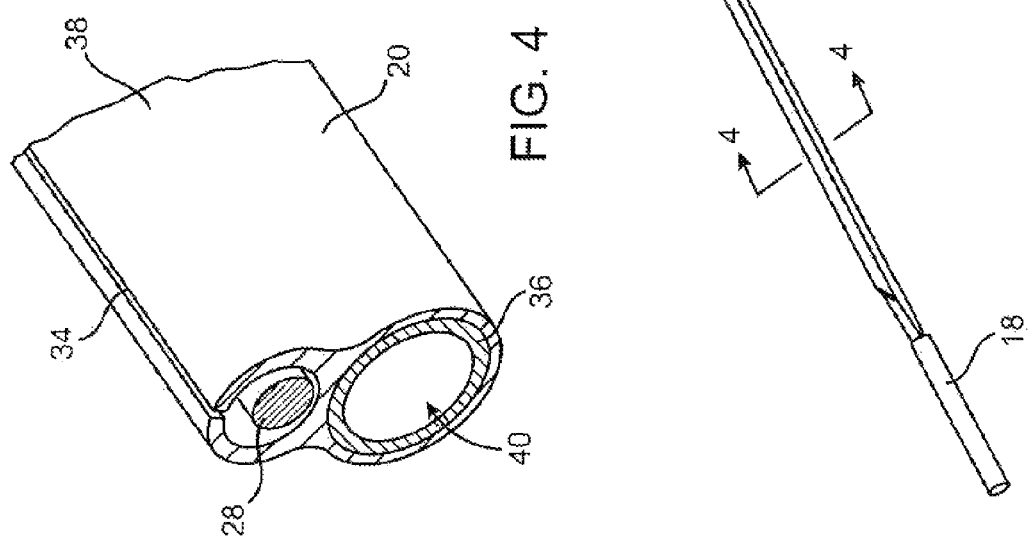

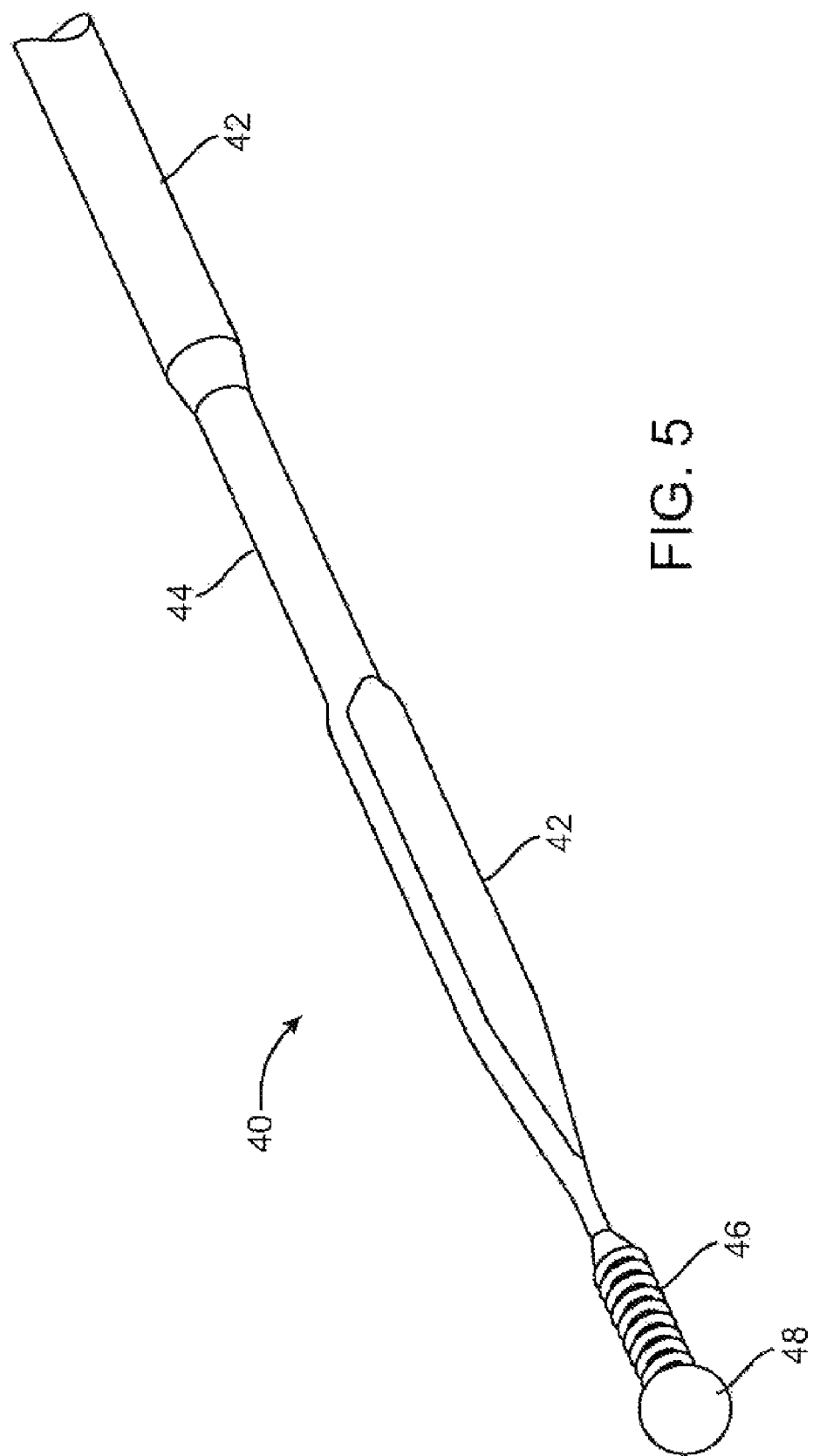

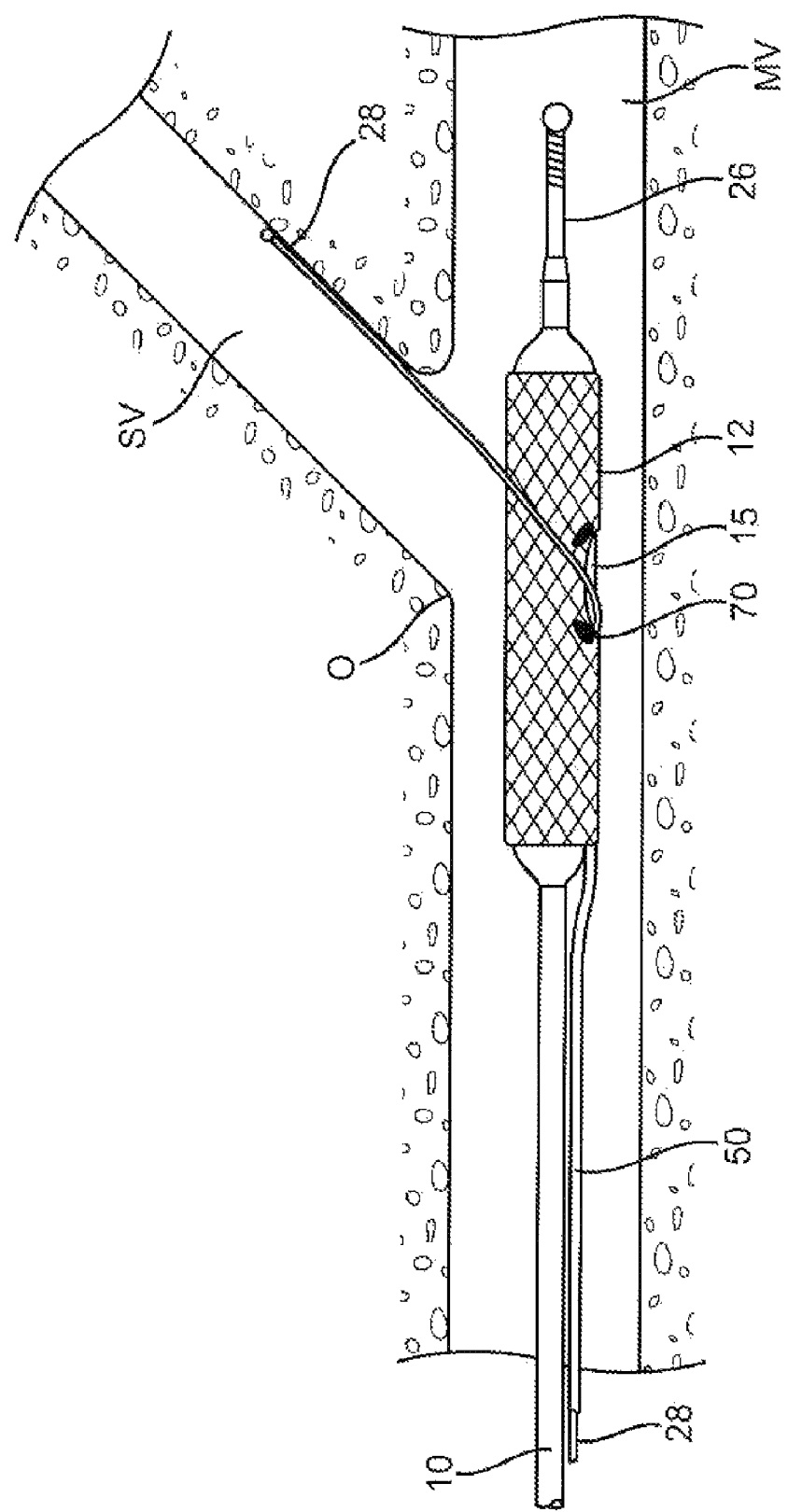

APPARATUS AND METHODS FOR DELIVERING PROSTHESES TO LUMINAL BIFURCATIONS

CROSS-REFERENCES TO RELATED APPLICATIONS

The present application claims benefit of U.S. Patent Application Ser. Nos. 60/672,735, filed Apr. 18, 2005 and 60/758,726, filed Jan. 12, 2006, the full disclosures of which are incorporated herein by reference.

BACKGROUND OF THE INVENTION

1. Field of the Invention

The present invention relates generally to medical devices and methods. More particularly, the present invention relates to apparatus and methods for delivering stents and other luminal prostheses to bifurcations in the vasculature and other body lumens.

Stenting is a common medical procedure used in the vasculature and other body lumens. Over the last decade, the use of stents and other vascular prostheses has become wide spread in the revascularzation of stenotic blood vessels where the blood vessel is first dilated and a stent placed to maintain vessel patency following the procedure. The stents are typically small, mesh-like tubular devices which are expanded in situ. They are typically formed from a metal and can be coated with drugs or other active agents.

The use of stents, and in particular drug-coated stents, has been very successful in the treatment of many forms for coronary artery disease. The success of stents, however, has been more limited for the treatment of lesions occurring at vessel bifurcations. While the disease in the main vessel is generally treated successfully, the outcome in the smaller or "side branch" vessel is often less successful. The lack of success is believed to result from a lack of coverage by the stent at the ostium (opening) of a lesion and the resulting lack of drug delivery to that area.

To overcome at least some of these shortcomings, the inventors herein have developed a stent having a self-opening side portion which covers the side branch ostium when the stent is opened in the main blood vessel or other body lumen. This stent is described in co-pending application Ser. No. 11/330,382, filed on Jan. 10, 2006, the full disclosure of which is incorporated herein by reference.

Stents having side holes or openings for alignment with side branch lumens are generally known in the art, and a variety of protocols and systems for delivering such stents to vascular and other luminal bifurcations are known. Of particular interest of the present invention, several guidewire systems have been proposed for delivering such stents to a luminal bifurcation and for aligning the side hole with a side branch ostium prior to expansion of the stent. For example, U.S. Pat. No. 5,749,825 to Fischell et al. describes introducing a balloon catheter carrying the stent over a main vessel guidewire. A side branch tube is positioned beneath a proximal portion of the stent and over the exterior of the balloon. A distal portion of the side branch tube extends through a side hole in the stent and permits advancement of a side branch guidewire into the side branch vessel. While generally effective for aligning the side hole of the stent with the side branch, the unconstrained distal portion of the side branch tube which extends from the side hole can interfere with advancement of the catheter through the vasculature. The presence of the side branch tube can increase the profile of the catheter, thus making it more difficult to introduce to smaller blood vessels and body lumens. Finally, Fischell suggests no specific approach for assuring that the two guidewires have not become crossed at the bifurcation so that the side hole is misaligned with the side branch ostium.

A similar stent and catheter structure is described in U.S. Pat. No. 6,048,361, to Von Oepen. The guidewire tube of the '361 patent (referred to as a "hollow chamber"), however, is shown to extend to the center of the side opening in the stent. While this reduces the likelihood that the guidewire tube will interfere with catheter advancement, the chance of such interference is not completely eliminated. The distal tip of the guidewire tube (hollow chamber) remains exposed through the side hole and can potentially impede advancement of the catheter.

Other patents showing the use of side tubes for delivering stents having side holes to bifurcated body lumens include U.S. Pat. No. 6,099,497; U.S. Pat. No. 6,165,195; and U.S. Pat. No. 6,596,020, and various related patents and publications.

Attempts have been made to design a dedicated stent for bifurcation lesions. These stent are designed to support and deliver drug to at least part of the bifurcation area.

However, current solutions usually require two balloons, two sheathes and two guide wires to facilitate both alignment and expansion of the stent.

These solutions suffer from a variety of shortcomings. One example of such shortcoming is high profile and cumbersome delivery system relatively to conventional stents, resulting in difficult delivery through tortuous anatomy and through tight lesions. It creates a need for aggressive predilation that causes trauma to the vessel.

Another example of such shortcoming is the need to deliver the device over two guide wires, when often the wires cross and prevent delivery. This may result in inability to deliver the stent and may cause damage to the vessel.

Another example of such shortcoming is due to the need for accurate axial and rotational positioning of the stent facing the side branch. These devices are mostly "self aligning," meaning that the stent is pushed to its axial position by the physician while rotational orientation is dictated by the side sheath. These devices do not provide indication for rotational orientation and do not provide the physician with means to torque the stent into position. Occasionally the high profile of these devices causes friction between the device and the lesion and may prevent the stent from aligning properly. Without means to torque the stent into position and without indication of proper position, the stent may be expanded with the side access facing the vessel wall instead of facing the side branch.

For these reasons, it would be desirable to provide improved apparatus, systems, and methods for delivering stents and other prostheses to bifurcated vasculature and other body lumens. In particular, it would be desirable to provide for the delivery of stents having a side opening such that the side opening is properly aligned with the ostium of a side branch lumen prior to expansion of the stent or other prostheses. It would be still more desirable if the delivery systems were compatible with stents having self-opening side structures in which to find the side opening in the stent. Such devices, systems, and methods should be compatible with small diameter (low profile) catheter structures, should reduce or eliminate any structure which exposed at or through the side openings in the stent or prostheses, and should allow for conformation of proper positioning of the side hole prior to expansion of the stent or other prostheses. At least some of these objectives will be met by the inventions described herein below.

2. Description of the Background Art

Patents and published applications describing bifurcated stents and delivery systems include U.S. Pat. Nos. 4,994,071; 5,609,627; 5,749,825; 5,755,735; 5,928,248; 6,048,361; 6,099,497; 6,165,195; 6,221,098; 6,210,429; 6,325,826; 6,596,020; 6,599,316; 6,676,691; 6,682,536; 6,689,156; 6,692,483; 6,709,440; 6,706,062; 6,835,203; 6,884,258; U.S. Publication Nos. 2002/0042650; 2002/0156516; 2002/0173835; 2003/0187494; 2003/0195606; 2004/0015227; 2004/0019302; 2004/0133268; 2004/0138737; 2005/0010278; 2005/0015108; 2005/0060027; 2005/0102,019; 2006/0036315; EP 1 2554 506 B1; and German Patents DE 297 08 803 U1; and DE 29 701 758 U1.

BRIEF SUMMARY OF THE INVENTION

The present invention provides apparatus and systems for the delivery of vascular and other luminal prostheses having side openings at bifurcations in the vasculature or other body lumens. Bifurcations will usually include a main branch vessel and a side branch vessel, where the cylindrical body of the prosthesis will be positioned within the main branch with the side opening aligned with an ostium or opening into the side branch. While the apparatus and systems will be particularly useful for delivering prostheses having self-opening side structures, as taught in co-pending U.S. patent application Ser. No. 11/330,382, the full disclosure of which has previously been incorporated herein by reference, it should be appreciated that they are also useful for delivering any stent or prosthesis having a side hole or other opening and/or side structure which is to be aligned with the ostium of a side branch.

In a first specific aspect of the present invention, a delivery catheter comprises a catheter shaft having a proximal end and a distal end, with an inflation hub or other inflation means attached to its proximal end. An expansion member, such as an inflatable balloon, is disposed near the distal end of the shaft, and an expandable prosthesis is mounted over the expansion member. The expandable prosthesis will typically be formed from a deformable metal so that expansion of the expansion member will enlarge the prosthesis from a small diameter configuration to a large diameter configuration which is anchored within the main vessel of the vasculature or other body lumen being treated. The prosthesis will further have a side hole, optionally in the form of a self-opening side structure, which is to be aligned with an ostium of the side branch lumen after the prosthesis has been expanded. The phrase "side hole" includes any opening or structure which is to be aligned with an ostium of a side branch lumen or vessel. The side hole may simply be a cell or a slit in the prosthesis structure which is preselected to be aligned with a side branch vessel but which is otherwise similar to other cells, slits, or the like in the prosthesis. More usually, however, the side hole will be an enlarged or enlargeable cell which is distinguishable from the adjacent or remaining structure of the prosthesis. In other embodiments, the "hole" comprises a self-opening or balloon openable peripheral structure which is intended to bridge the circumference of the side branch ostium after the prosthesis is opened in the main branch. Such alignment is achieved with a guidewire structure which is disposed over the expansion member (optionally over or within the folds of an inflatable balloon) and beneath a proximal portion of the prosthesis. In an initial configuration of the catheter, the guidewire structure will extend to a holding location which is spaced proximally from the side hole of the prosthesis, usually by a distance of at least 1 mm, preferably at least 2 mm, and more preferably at least 3 mm.

The guidewire structure may have a variety of configurations. In one specific embodiment, the guidewire structure comprises a guidewire tube which carries the guidewire in a lumen thereof. The guidewire tube will be positioned between the prostheses and the expandable member, as just described, and the guidewire will remain in the guidewire tube with a distal end retracted fully within the tube during advancement of the catheter to a position near the bifurcation. In an alternative embodiment, the guidewire structure may comprise an elongate slide having a channel which slidably receives the guidewire. The channel can be formed, for example, as a "half tube" with an open top which can be oriented either toward the balloon or toward an inner surface of the prosthesis. The use of a slide may be preferred over the use of a full guidewire tube since it can reduce the resulting profile or diameter of the catheter. As a second alternative, the guidewire structure may consist essentially or only of the guidewire itself. That is, the guidewire may be directly placed between the inner surface of the prosthesis and the outer surface of the expandable member without any further structure surrounding it. In all cases, however, the guidewire and any other structure associated with the guidewire will be withdrawn proximally of the side hole by the requisite distances described above.

The delivery catheters of the present invention will preferably further comprise a central guidewire extending distally from the catheter shaft. In some instances, the central guidewire could be fixed to (combined and immobilized with) the catheter shaft, but more often the central guidewire will be a conventional moveable guidewire, either in a over-the-wire design (which extends fully or almost fully through the entire catheter shaft), in a rapid exchange design where the guidewire extends only through a distal portion of the catheter shaft, or in other conventional simplified exchange designs.

In a second aspect of the present invention, a delivery catheter comprises a catheter shaft, an expansion member, and an expandable prosthesis having a side hole, generally as described above. The guidewire is disposed over the expansion member and beneath at least a proximal portion of the prosthesis so that the guidewire is advanceable through the side hole. In this particular embodiment, the guidewire may extend partially or fully to side hole and in some instances through the side hole of the prosthesis even while the catheter is being advanced through the vasculature toward the bifurcation. In this aspect of the invention, the catheter shaft includes a split lumen along at least a portion of its length for removably receiving a proximal portion of the side guidewire. The split lumen is particularly useful for constraining the side guidewire in embodiments where a main guidewire is received only in a distal portion of the catheter shaft (typically to facilitate rapid exchange). In such instances, the side guidewire could become entangled or twisted with the main guidewire if both guidewires were free of the catheter shaft structure. The split lumen would preferably be used to constrain the side guidewire, but could be used for the main or the side guidewires. In other embodiments, it would be possible to enlarge the split lumen to receive both wires or to provide two split lumens for receiving both the main guidewire and the side guidewire.

Other features of the delivery catheter having the split guidewire lumen are generally the same as those described in connection with the first aspect of the present invention. The delivery catheter will usually comprise a central guidewire, either a fixed central guidewire or moveable central guidewire. The side guidewire may be received in a guidewire tube, in a guidewire slide, or maybe disposed directly between the expandable member and an inner surface of the prosthesis. In this aspect of the invention, the guidewire and any other guidewire structure may also extend through the side hole in the prosthesis even when the catheter is in its delivery configuration for advancement through the main vessel.

In a third aspect of the present invention, methods are provided for delivering a prosthesis having a side hole (as defined above) to a luminal location. The methods comprise advancing a catheter over a central guidewire through a main lumen, such as an artery or other blood vessel, to position the prosthesis near the bifurcation. A side guidewire is then advanced through the side hole into a branch lumen of the bifurcation, and the prosthesis is eventually expanded at the bifurcation with the side hole aligned with the side branch. In order to assure that the side hole is properly aligned with the ostium or opening of the side branch, radiopaque markers are provided on the prosthesis and/or on the guidewire so that the positions may be observed under fluoroscopy. If it is observed that the catheter is rotated so that the guidewire crosses the prosthesis to reach the side branch, or the side hole is directed away from the ostium, then it is clear that the side hole is not properly aligned with the side branch ostium. Thus, the catheter may be rotated until it is apparent under the fluoroscopic imaging that the guidewire is no longer crossing the prosthesis and the side hole is therefore rotationally aligned with the side branch ostium. Rotation is achieved by applying torque on the device through the hub. In order that the device distal area will rotate in conjunction to the rotation of the hub the catheter needs to transmit torque effectively. This can be achieved by the use of torque resistant shafts, such as metal shaft for the proximal catheter area and braided or otherwise stiffened shafts for the distal area.

This method for rotationally aligning the prosthesis is compatible with any of the catheter systems described previously where the side guidewire extends through the side hole of the prosthesis to aid in alignment of the side hole with the side branch ostium, including systems which require a separate balloon to deploy a side structure on the prosthesis into the ostium of the side branch.

BRIEF DESCRIPTION OF THE DRAWINGS

FIG. 3 is an enlarged view of a proximal portion of the delivery catheter of FIG. 1.

FIG. 4 is a cross-sectional symmetric view taken along line 4-4 of FIG. 3.

FIG. 5 illustrates a side guidewire which is useful in the apparatus and methods of the present invention.

FIGS. 10A and 10B illustrate an optional aspect of the method of the present invention for assuring that the side guidewire does not cross the prosthesis as the prosthesis is expanded.

DETAILED DESCRIPTION OF THE INVENTION

Figure 1:
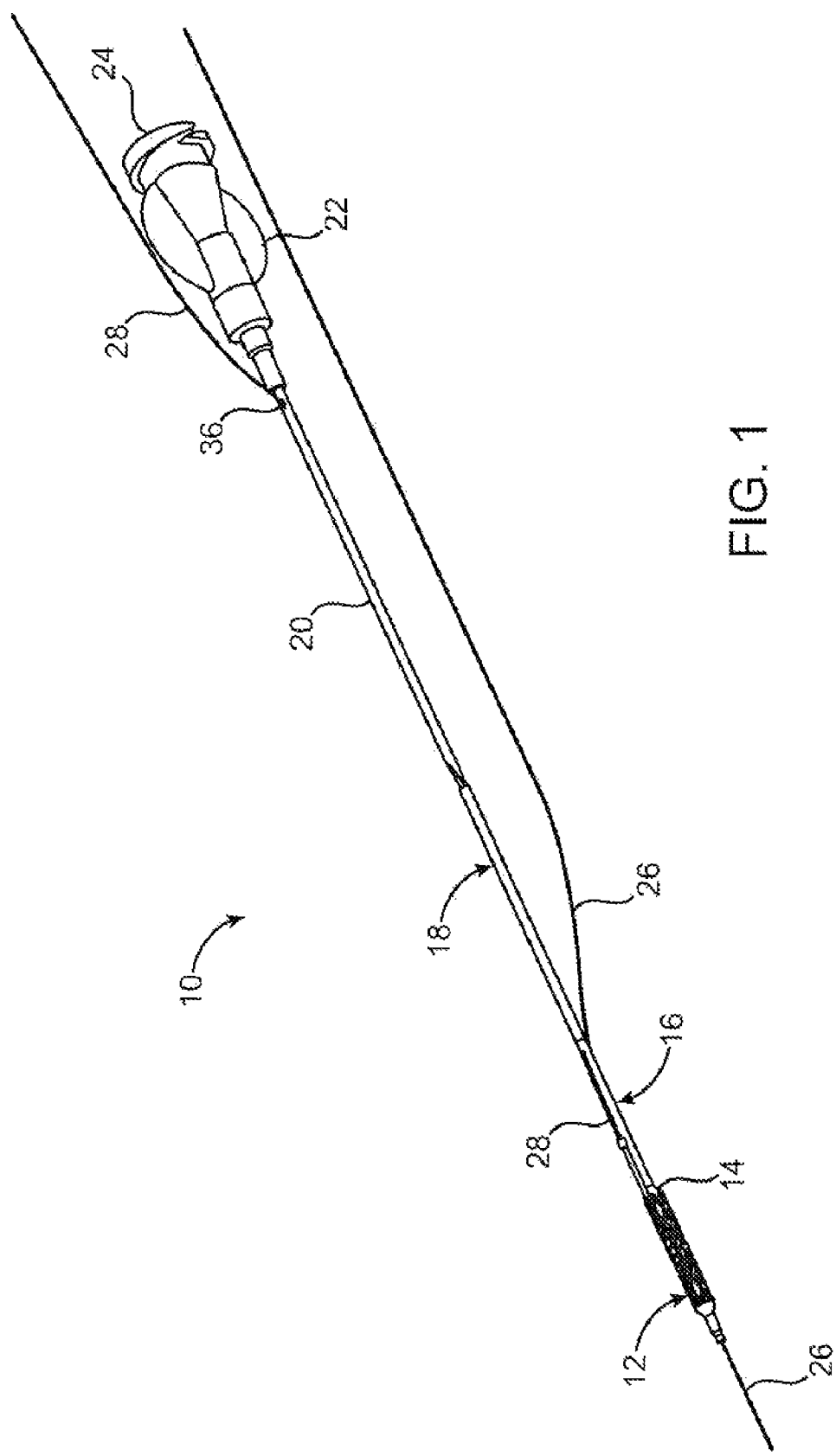
FIG. 1 is an isometric view of a delivery catheter constructed in accordance with the principles of the present invention.

Referring now to FIG. 1, a delivery catheter 10 carries a prosthesis 12 having a side hole 15 (FIG. 2) on an expandable member 14, such as an inflatable balloon of the type normally employed in stent delivery. The delivery catheter 10 further comprises a distal section 16, an intermediate section 18, and a proximal section 20, where the sections are arranged to provide an elongate catheter body to support the expandable member 14 so that it may be delivered intraluminally or intravascularly to a target site in a generally conventional manner. Typically, the distal and intermediate sections 18 will be relatively more flexible than the proximal section 20. A proximal hub 22 having a connector 24 for connection to a balloon inflater is attached to a proximal end of the proximal section 20. The hub can have any design including a y-shaped hub, a hub with flexible connector, and the like. A central guidewire 26 is received through the balloon and exits from a port near the proximal end of distal section 16 of the catheter body. Although illustrated as a "rapid exchange" design, it will be appreciated that the shaft of the delivery catheter 10 could also be adapted for over-the-wire introduction over the central guidewire 26, or any other know or future design.

Figure 2:
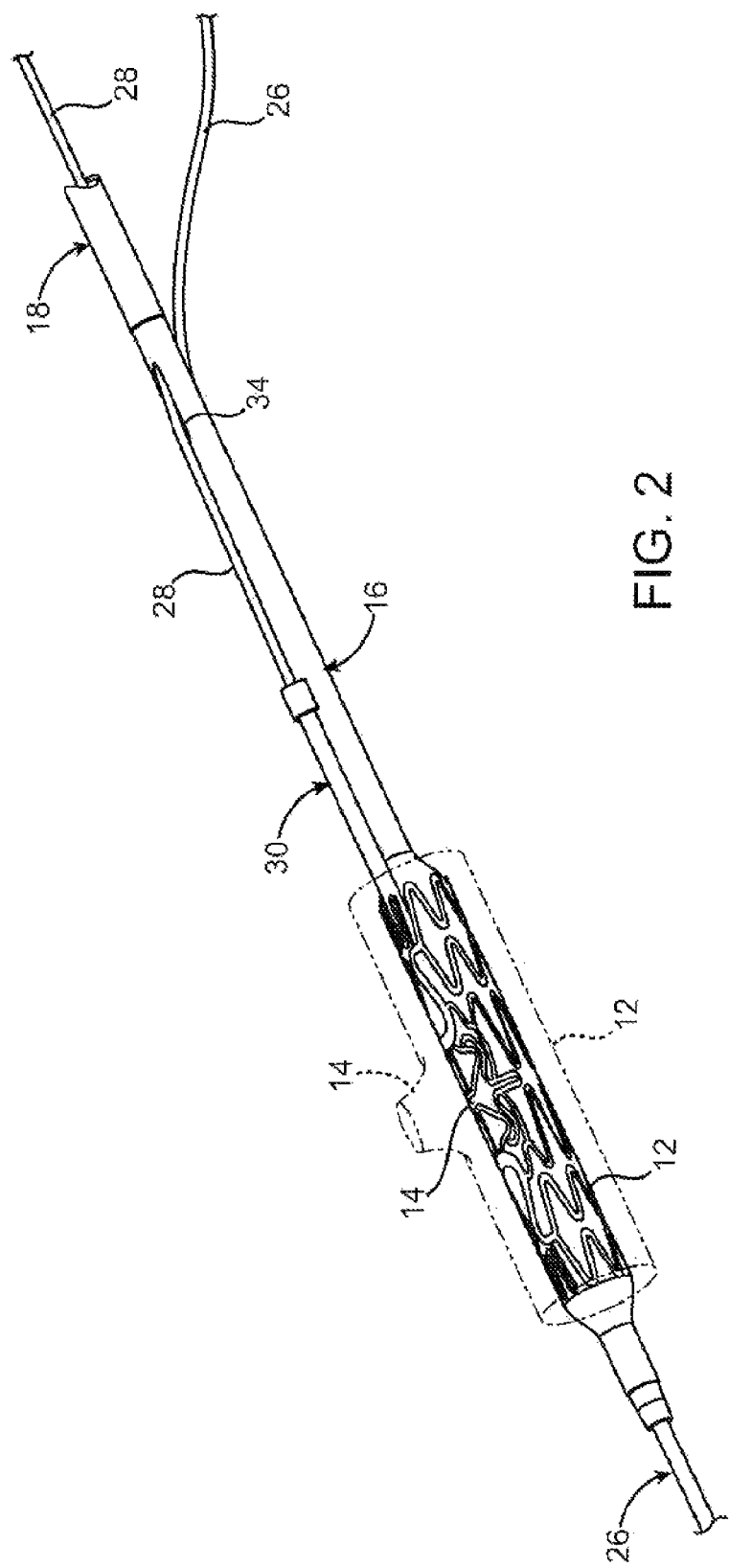
FIG. 2 is an enlarged view of a distal portion of the catheter of FIG. 1, shown with an expanded prosthesis in broken line.

Of particular interest to the present invention, a side guidewire 28 is disposed beneath a proximal portion of the prosthesis 12 and over the expandable member 14. As described in more detail in connection with FIGS. 6-8, the side guidewire may be disposed in a guidewire tube, guidewire slide, or without further supporting structure. As shown in FIG. 2, the side guidewire 28 is disposed in a guidewire tube 30 which extends beneath the prosthesis 12. The side guidewire 28 passes into a lumen within the catheter shaft through a port 34 and passes back out of the shaft through a proximal port 36 (FIG. 1). The prosthesis 12 will have a side hole 15, preferably in the form of a self-opening or other side structure, as shown in broken line in FIG. 2. Details of a self-opening side structure are provided in copending application Ser. No. 11/330,382, the full disclosure of which has previously been incorporated herein by reference.

Referring now to FIGS. 3 and 4, the proximal section 20 of the delivery catheter may optionally be formed with a split side lumen 34 for removably receiving the side guidewire 28, as best seen in FIG. 4. This section can be formed over a hypotube 36 with a polymeric extrusion 38 over the hypotube forming the split guidewire lumen 34. Open lumen 40 through the hypotube will serve as the inflation lumen for the catheter. The split side guidewire lumen is particularly advantageous since it allows the guidewire to be constrained during advancement of the catheter. By constraining the side guidewire, the chance of crossing or otherwise entangling the side guidewire 28 with the main guidewire 26 is greatly reduced. It would be possible, of course, to provide a second split guidewire for the main guidewire, or in other instances deeming guidewire could be received within a central lumen of the catheter shaft in a conventional over-the-wire configuration. In alternative embodiments, the polymeric tube may be extended separately and may be separate from the hypotube.

Referring now to FIG. 5, an exemplary side guidewire 40 comprises a round proximal section 42, a reduced diameter round transition section 44, and a flat distal section 42. A radiopaque coil 46 joins the distal end of the flat section 42 optionally with an atraumatic distal sphere 48. The guidewire can be formed from stainless steel, shape memory materials, or other conventional guidewire materials, and will have dimensions normally associated with guidewires for intravascular or other luminal uses. The delivery catheters of the present invention can be used with a variety of other guidewires, including very low profile guidewires which can further reduce the diameter of the catheter system.

Figure 6A:
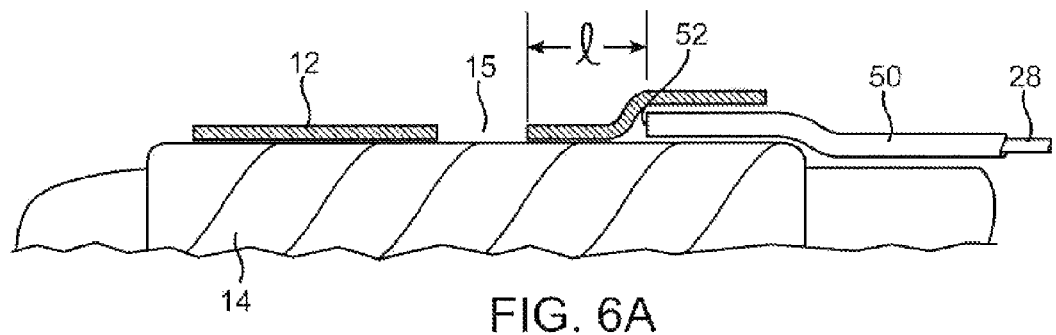
FIGS. 6A and 6B illustrate positioning of a guidewire tube beneath a prosthesis mounted on an expandable member in accordance with the principles of the present invention.
Figure 6B:
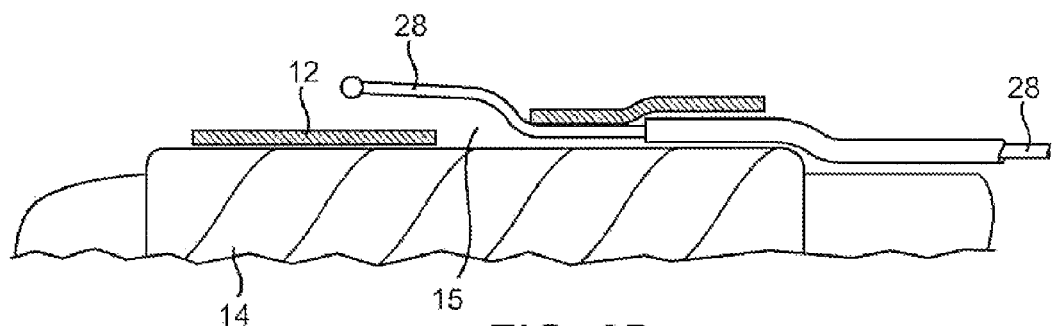

Referring now to FIGS. 6 through 8, positioning of the side guidewire 28 beneath a proximal portion of prosthesis 12 and over the expandable member 14 will be described for several embodiments of the present invention. In the embodiment of FIGS. 6A and 6B, guidewire 28 is disposed in a guidewire tube 50 which is located beneath a proximal portion of the prosthesis 12 and over an outer surface of the expandable member 14. A distal tip 52 of the guidewire tube is located by a minimum distance l from the closest point of the side hole 15. The distance l will generally be at least 1 mm, preferably being at least 2 mm, and often being 3 mm or more. In the catheter introduction configuration, the guidewire 28 will be fully retracted within the guidewire tube 50, as shown in FIG. 6A. Once the catheter has been advanced to the bifurcation, the guidewire 28 may be advanced distally and through the opening 15 so that it may be guided to the side branch, as shown in FIG. 6B.

Figure 7A:
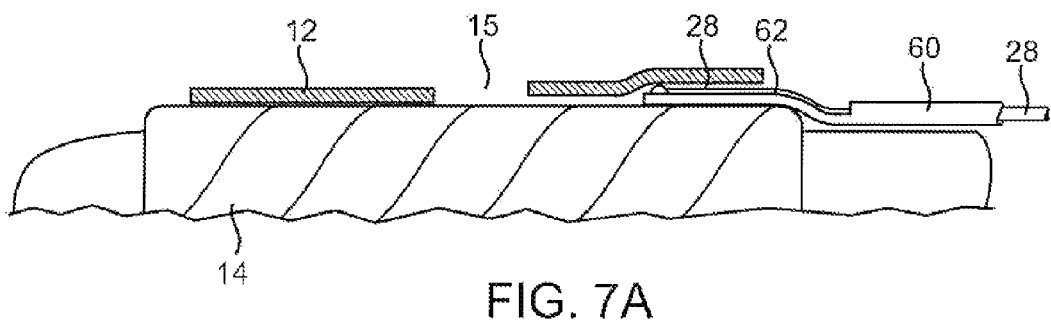
FIGS. 7A and 7B illustrate positioning of a guidewire slide positioned beneath the prosthesis and over an expandable member in accordance with the principles of the present invention.
Figure 7B:
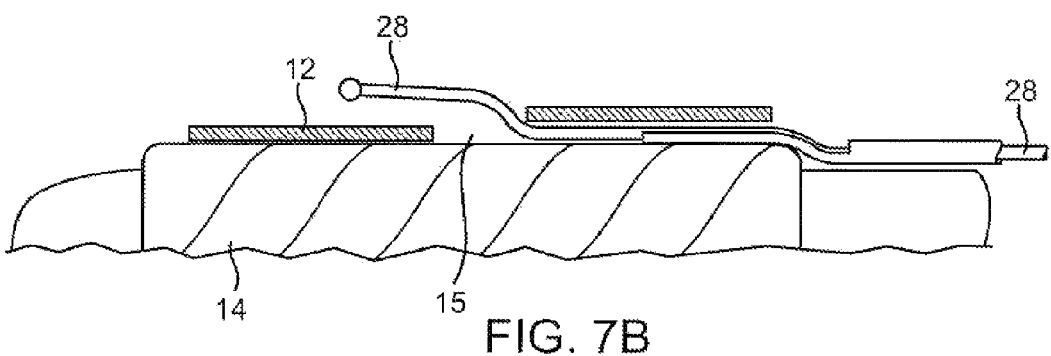

In a first alternative embodiment as shown in FIGS. 7A and 7B, the side guidewire 28 may be disposed in a guidewire slide 60 having a region 62 which is open on the side adjacent the prosthesis 12. Thus, the guidewire 28 may be received in a channel formed by the open region of the slide 60 which provides a guide to help advance the guidewire through the opening 15, as shown in FIG. 7B. As with the previous embodiment, the distal most end of the guidewire 28 and guidewire slide 60 will be maintained by the minimum distance l from the closest portion of the opening 15.

Figure 8A:
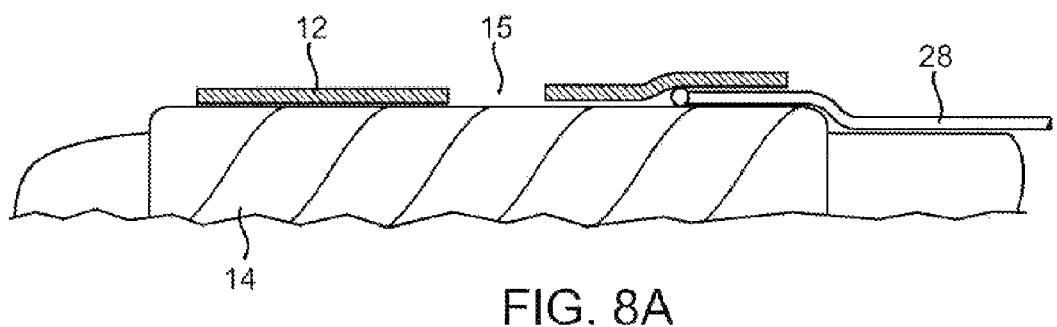
FIGS. 8A and 8B illustrate a guidewire which is positioned without additional supporting structure beneath a prosthesis and over and expandable member in accordance with the principles of the present invention.
Figure 8B:
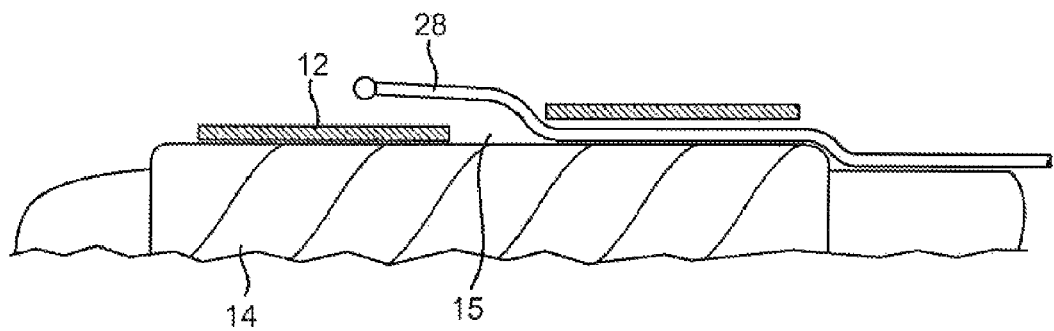

In a second alternative embodiment, guidewire 28 may be disposed directly between the inner surface of the prosthesis 12 and the outer surface of the expandable member 14, as shown in FIGS. 8A and 8B. Again, the distal tip of the guidewire 28 will be maintained at a minimum distance l from the closest portion of the opening 15 in the prosthesis. Once the catheter has been advanced to a location near the bifurcation, the side guidewire may be advanced through the opening, as shown in FIG. 8B.

Figure 9A:
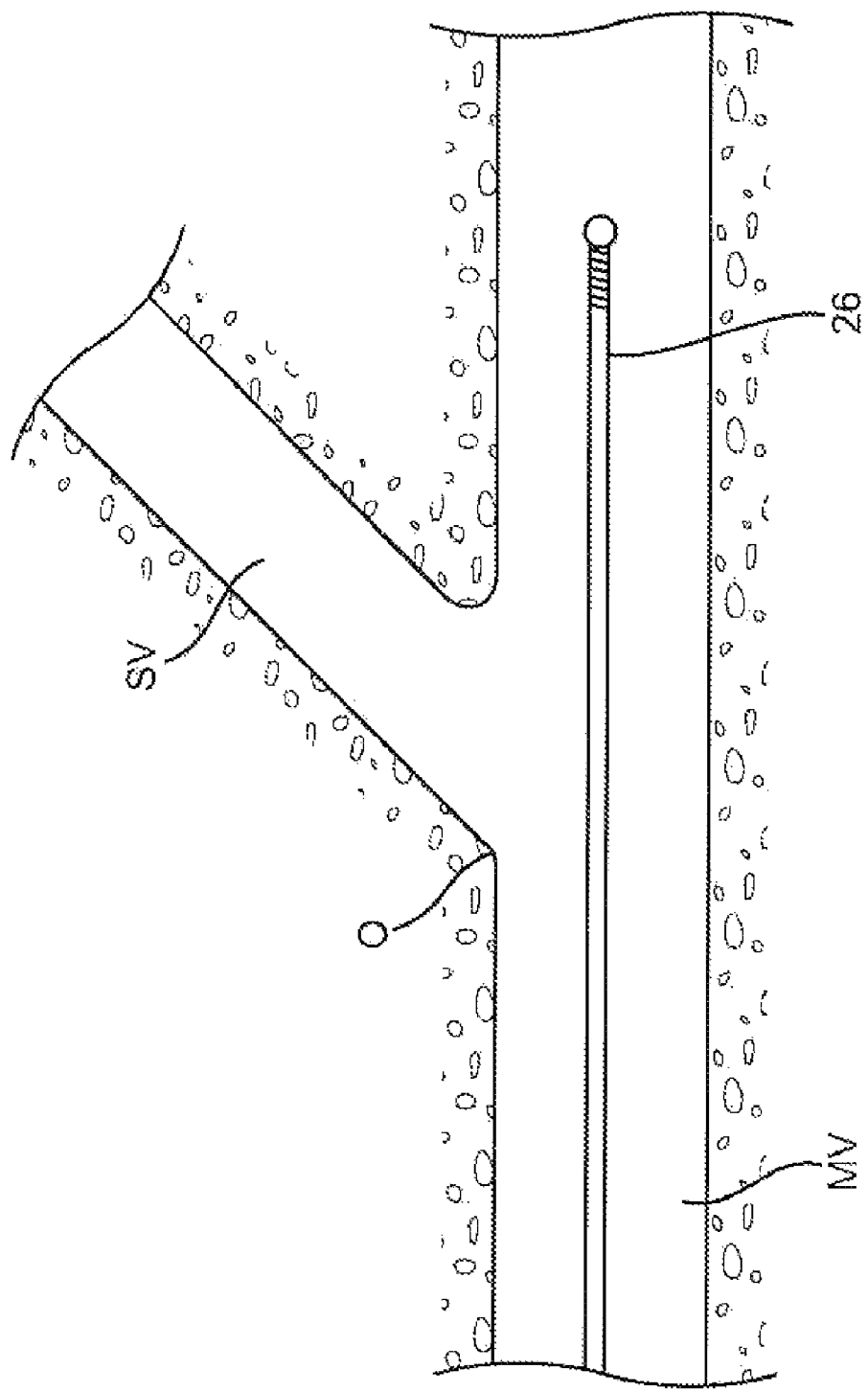
FIGS. 9A through 9E illustrate use of the delivery catheters of the present invention for implanting a prosthesis having a side hole at an ostium of a side branch in the vasculature of a patient in accordance with the principles of the present invention.
Figure 9B:
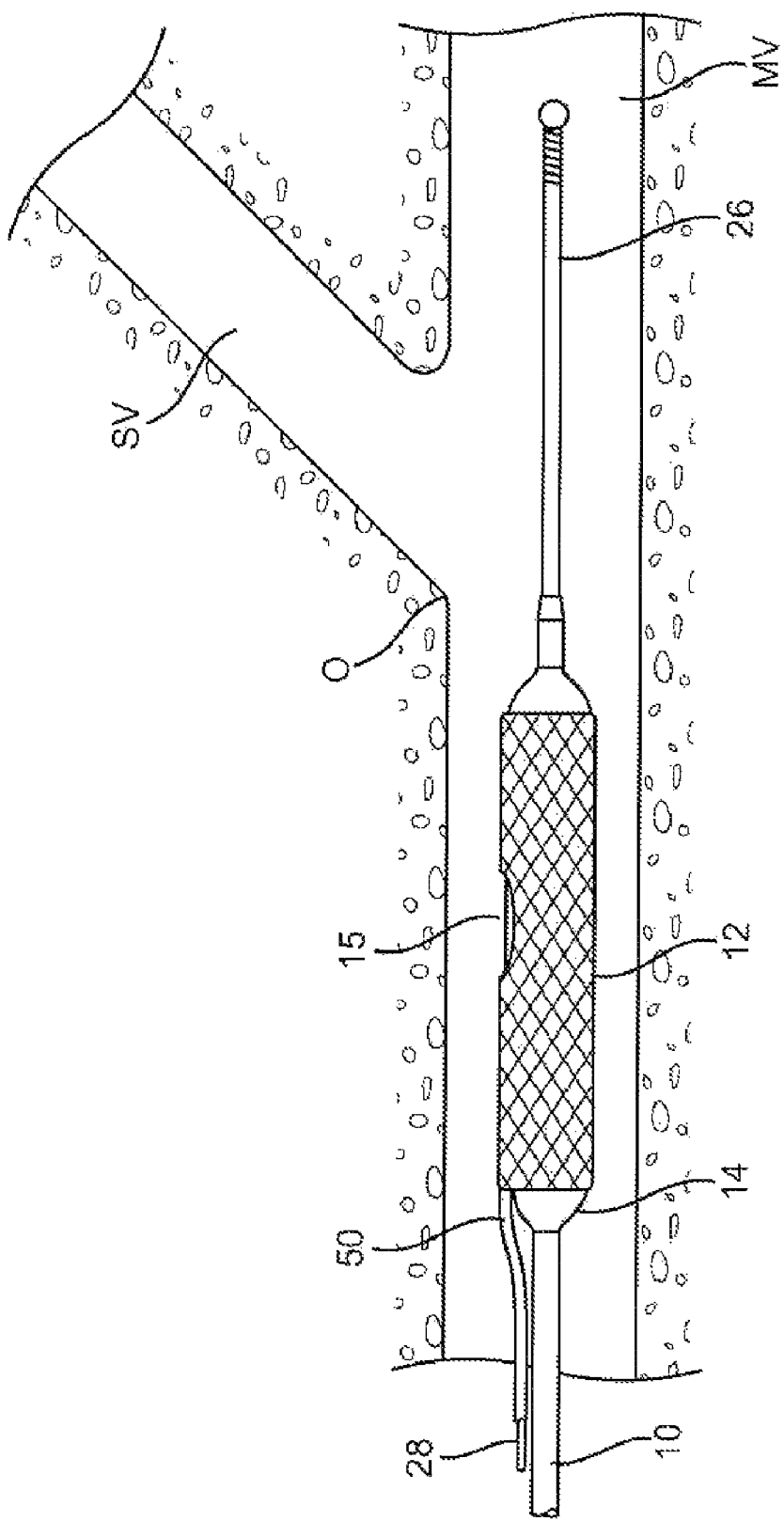

Referring now to FIGS. 9A through 9E, an example of the delivery of prosthesis 12 using the delivery catheter 10 to a branch lumen comprising a main vessel MV and a side vessel SV will be described. First, the central guidewire 26 is advanced through the main vessel to a point beyond the ostium O of the side vessel SV, as shown in FIG. 9A. The catheter 10 may be advanced over the central guidewire 26 in the conventional manner until the prosthesis 12 approaches the ostium O of the side vessel SV. In FIG. 9B, the side guidewire 28 is shown in the guidewire tube 50, but it will be appreciated that any of the guidewire structures of FIGS. 6-8 could be employed.

Figure 9C:
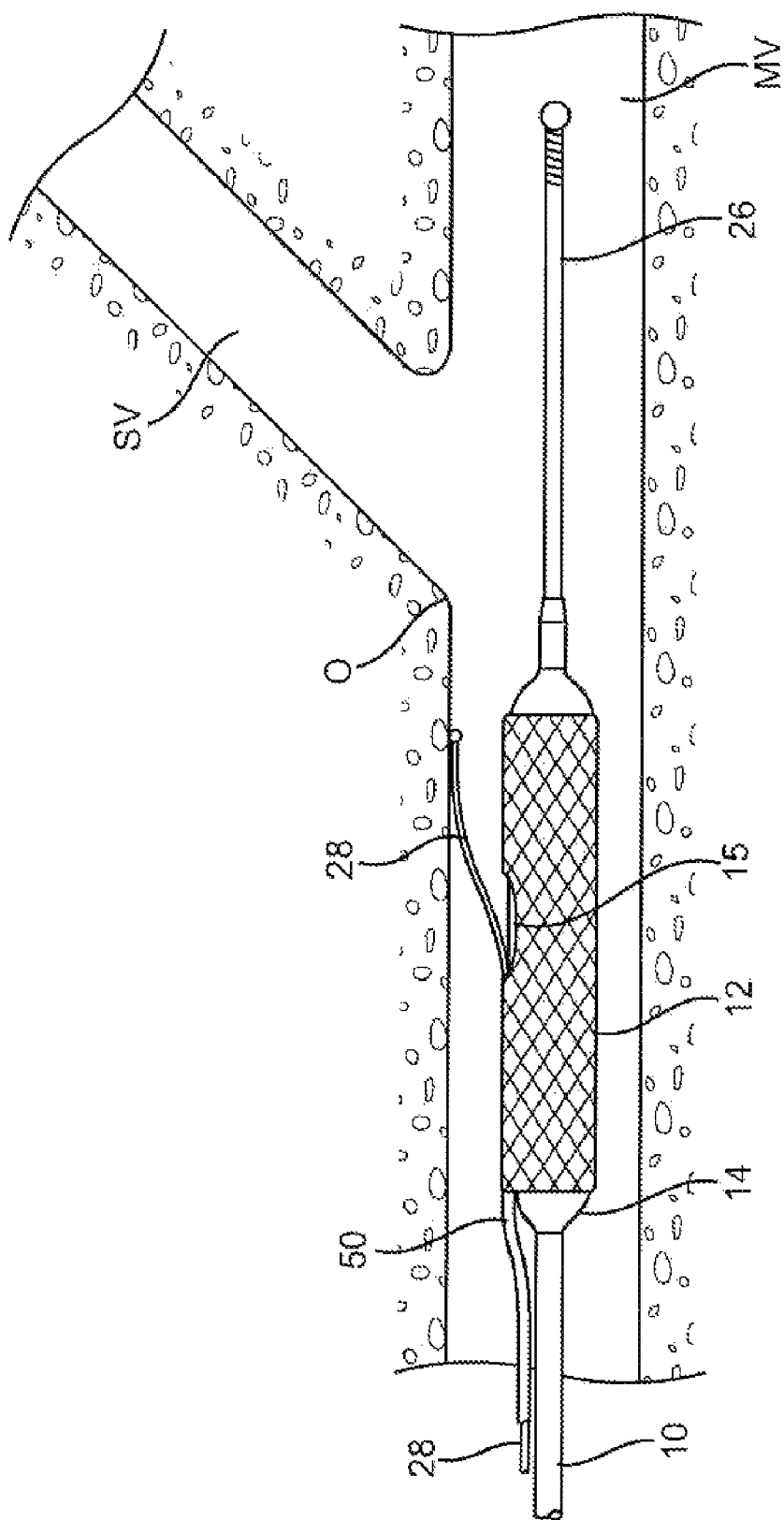
Figure 9D:
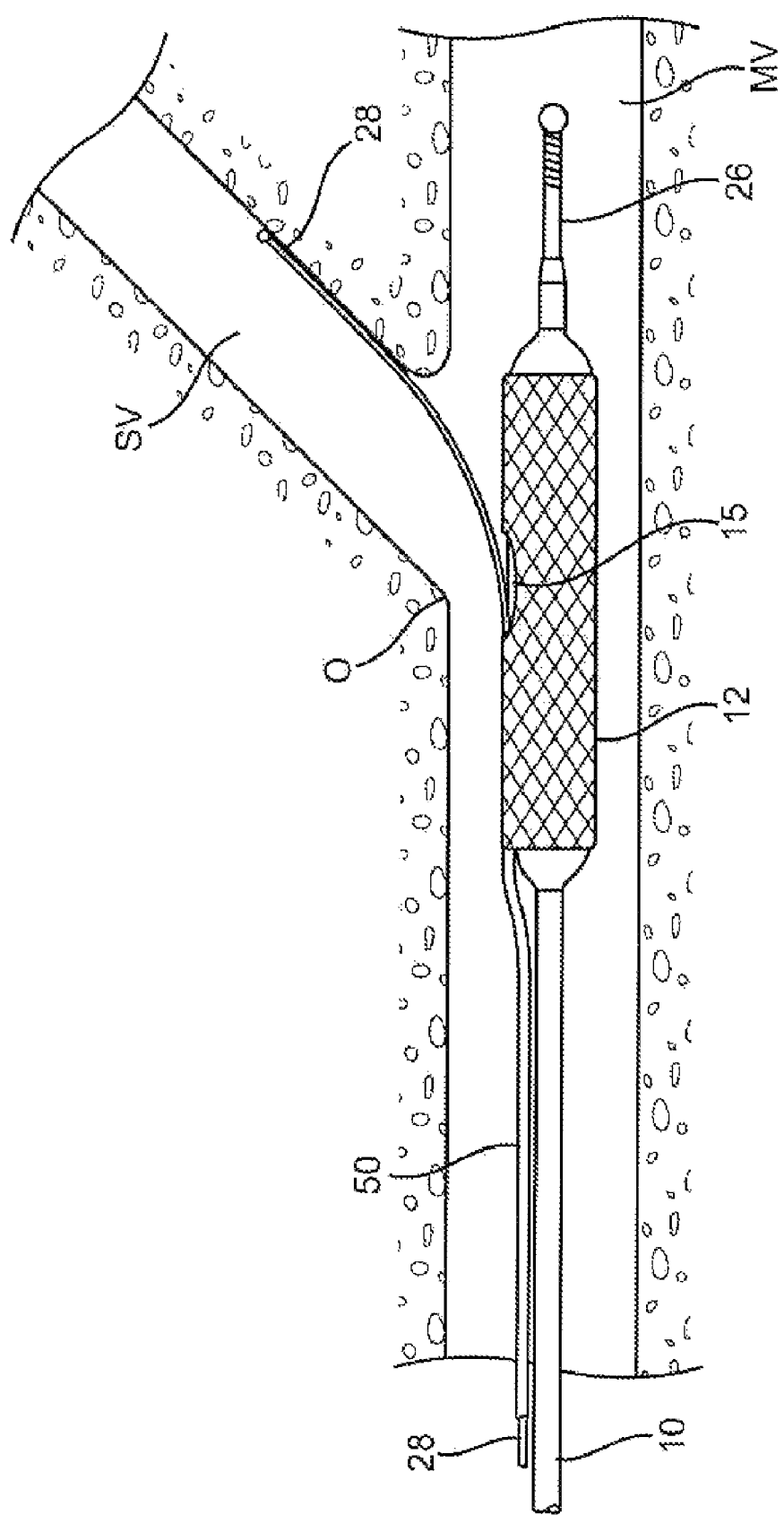
Figure 9E:
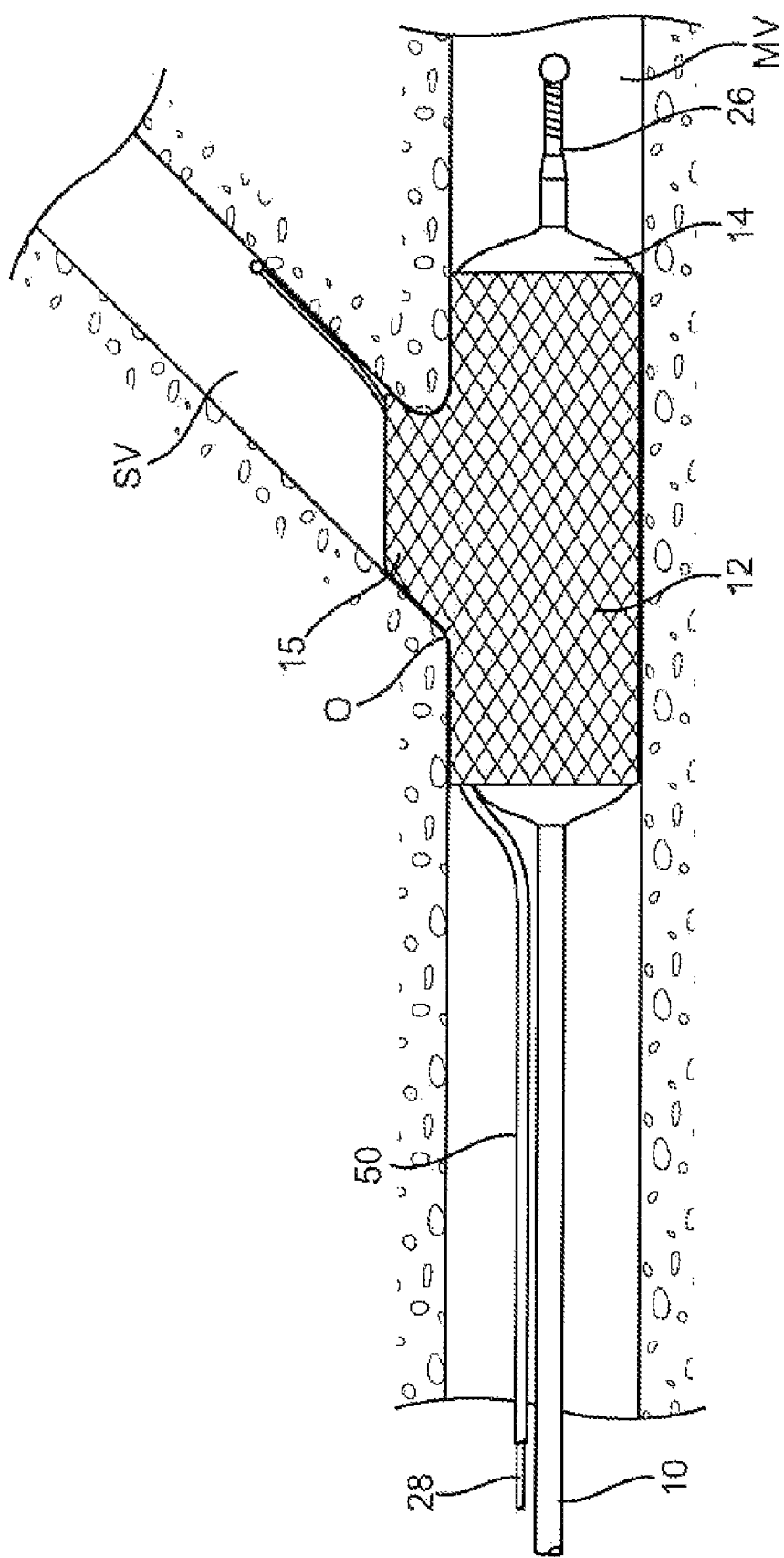

The side guidewire 28 is next distally advanced through the opening 15 of prosthesis 12, as shown in FIG. 9C, and the guidewire is then advanced through the ostium O and into the side vessel SV, as shown in FIG. 9D. At that point, the catheter may be advanced so that the opening 15 in the prosthesis 12 approaches and eventually aligns with the ostium O. The balloon or other expandable member 14 may then be inflated so that the prosthesis 12 expands within the main vessel MV and the side opening (shown as a self-opening side structure) aligns with the ostium O, as shown in FIG. 9D. In one embodiment, the side guidewire will have a stiffer section near its distal end to improve system alignment.

Figure 10B:
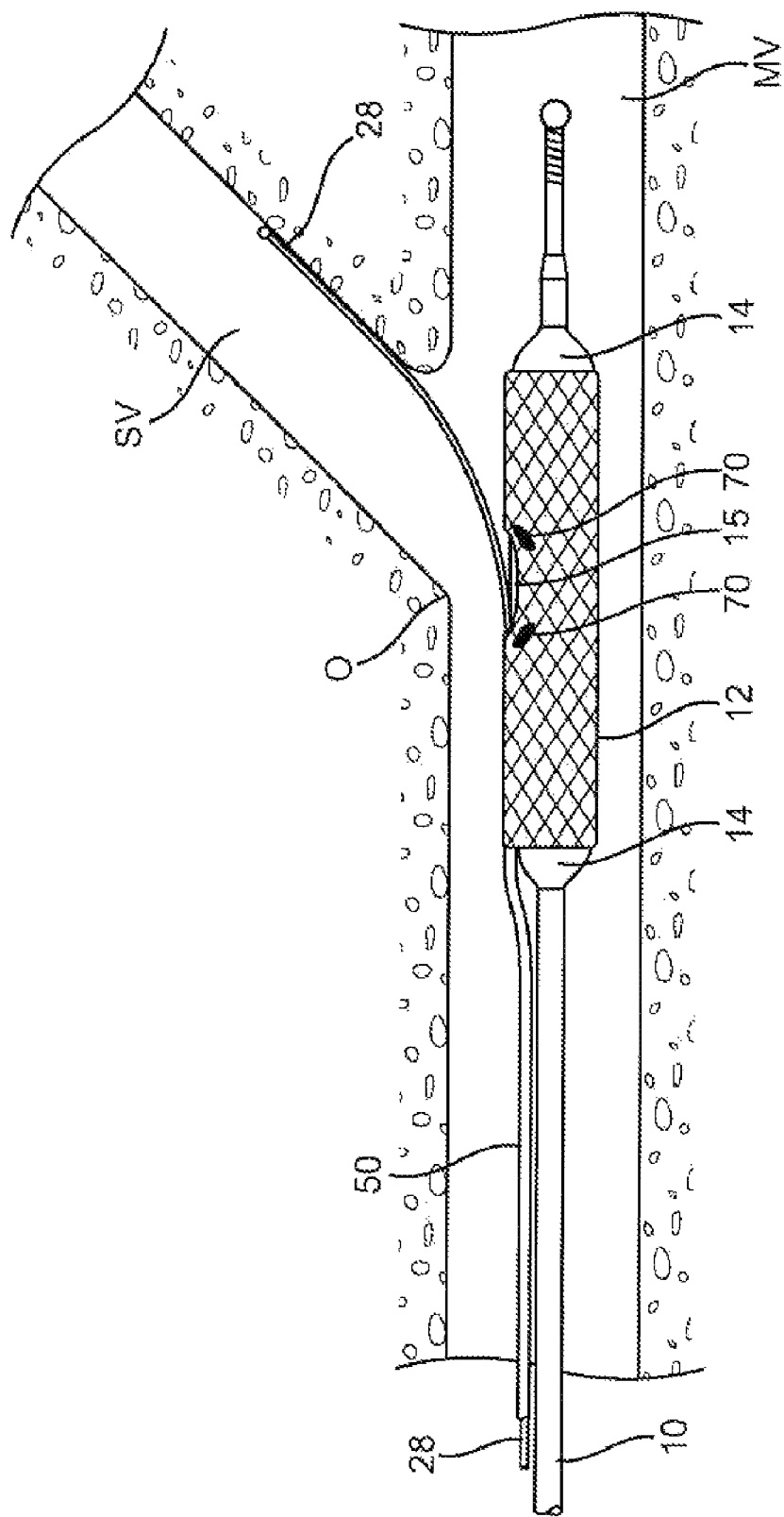

In a preferred aspect of the present invention, the side guidewire 28 may be radiopaque (or include radiopaque markers) and/or radiopaque markers may be provided on a side of the prosthesis 12 aligned with the side opening 15. The use of such radiopaque structures allows the physician to easily determine whether the prosthesis is rotationally misaligned with the ostium O of the side vessel SV. As shown in FIG. 10A, when the prosthesis is rotationally misaligned, the side guidewire will extend across the prosthesis 12. Expansion of the prosthesis 12 in this position will of course not result in alignment of the side opening 15 with the ostium O. In cases where a separate balloon is used to deploy a side structure, such misalignment can dissect or perforate the artery or other treated lumen. The catheter can then be torqued to rotate the prosthesis 12 so that the opening 15 is adjacent the ostium O with the side guidewire 28 positioned as shown in FIG. 10B. This configuration is readily observed under fluoroscopic imaging since the radiopaque markers 70 on the prosthesis 12 (generally adjacent to the opening 15) will be adjacent to the ostium O. Additionally, the radiopaque side guidewire 28 can be observed going directly from the opening into the side branch vessel SV. In this configuration, the prosthesis may be deployed by expanding the expandable member 14.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A method for delivering a prosthesis having a side hole to a luminal bifurcation, said method comprising:
   advancing a catheter over a central guidewire through a main lumen to position the prosthesis near the bifurcation;
   advancing a side guidewire through the side hole into a branch lumen at the bifurcation;
   observing radiopaque markers on the side guidewire to determine if the side guidewire is crossing the prosthesis to reach the side branch;
   if the side guidewire is crossing the prosthesis, rotating a proximal end of the catheter to rotate the prosthesis until the side guidewire no longer crosses the prosthesis; and
   expanding the prosthesis at the bifurcation with the side hole aligned with the side branch.

2. A method as in claim 1, wherein the guidewire had been fully retracted beneath the prosthesis while the catheter had been initially advanced over the central guidewire.

3. A method as in claim 1, wherein the side guidewire is advanced through a guidewire tube which passes over an expansion member and beneath a proximal portion of the prosthesis.

4. A method as in claim 1, wherein the side guidewire is advanced through a channel in an elongate slide which passes over an expansion member and beneath a proximal portion of the prosthesis.

5. A method as in claim 1, wherein the side guidewire is positioned directly between an expansion member and an inner surface of the prosthesis prior to advancing.

6. A method as in claim 1, wherein expanding the prosthesis comprises expanding an expansion member within the prosthesis.

7. A method as in claim 6, further comprising deflating the expansion member, wherein deflating the expansion member releases the side guidewire from the side hole.

8. A method as in claim 1, wherein rotating the catheter comprises rotating a hub attached to the proximal end of the catheter.

9. A method for delivering a prosthesis having a side hole to a luminal bifurcation, said method comprising:

advancing a catheter to position the prosthesis near the bifurcation, wherein the catheter is positioned over a central guidewire in a main branch lumen and a side branch guidewire extends through the side hole into a side branch lumen;

observing radiopaque markers on the side branch guidewire to determine if the side branch guidewire is crossing the prosthesis or central guidewire to reach the side branch;

if the side branch guidewire is crossing the prosthesis or the central guidewire, rotating a proximal end of the catheter to rotate the prosthesis until the side branch guidewire no longer crosses the prosthesis or central guidewire; and expanding the prosthesis at the bifurcation with the side hole aligned with the side branch.

10. A method as in claim 9, wherein the side guidewire is fully retracted beneath the prosthesis while the catheter is advanced over the central guidewire.

11. A method as in claim 10, further comprising advancing the side guidewire through a guidewire tube which passes over an expansion member and beneath a proximal portion of the prosthesis.

12. A method as in claim 9, further comprising advancing the side guidewire through a channel in an elongate slide which passes over an expansion member and beneath a proximal portion of the prosthesis.

13. A method as in claim 9, further comprising advancing the side guidewire while said side guidewire is positioned directly between an expansion member and an inner surface of the prosthesis prior to advancing.

14. A method as in claim 9, wherein expanding the prosthesis comprises expanding an expansion member within the prosthesis.

15. A method as in claim 14, further comprising deflating the expansion member, wherein deflating the expansion member releases the side guidewire from the side hole.

16. A method as in claim 9, wherein rotating the catheter comprises rotating a hub attached to the proximal end of the catheter.

* * * * *